United States Patent

Preusser et al.

[11] Patent Number: 4,664,783
[45] Date of Patent: May 12, 1987

[54] METHOD FOR THE SEPARATION OF AROMATES FROM HYDROCARBON MIXTURES CONTAINING AROMATICS

[75] Inventors: Gerhard Preusser, Essen; Martin Schulze, Neviges, both of Fed. Rep. of Germany

[73] Assignee: Krupp-Koppers GmbH, Essen, Fed. Rep. of Germany

[21] Appl. No.: 708,331

[22] Filed: Mar. 5, 1985

[30] Foreign Application Priority Data

Mar. 13, 1984 [DE] Fed. Rep. of Germany ....... 3409030

[51] Int. Cl.$^4$ .................. C07C 7/08; C10G 21/20; C10G 21/28
[52] U.S. Cl. .................................... 208/313; 208/321; 208/326; 585/804; 585/808
[58] Field of Search ............... 208/313, 321, 326, 333, 208/DIG. 1; 585/808, 804, 807, 860, 863

[56] References Cited

U.S. PATENT DOCUMENTS

| 2,902,444 | 9/1959 | Shmidl | 208/333 |
| 3,107,501 | 1/1965 | Woodle | 208/313 |
| 3,788,980 | 1/1974 | Kubek et al. | 208/333 |
| 3,816,302 | 6/1974 | Paret | 208/326 X |
| 3,819,917 | 6/1974 | Sweeney, Jr. et al. | 208/DIG. 1 |
| 4,081,355 | 3/1978 | Preusser et al. | 585/808 |
| 4,125,458 | 11/1978 | Bushnell et al. | 208/321 X |
| 4,278,505 | 7/1981 | Danulat et al. | 208/313 X |

FOREIGN PATENT DOCUMENTS

| 154677 | 9/1985 | European Pat. Off. | 585/808 |
| 1444357 | 3/1962 | Fed. Rep. of Germany . | |
| 1468173 | 6/1970 | Fed. Rep. of Germany . | |
| 1119292 | 7/1968 | United Kingdom . | |

Primary Examiner—Glenn Caldarola
Attorney, Agent, or Firm—Michael J. Striker

[57] ABSTRACT

A method is disclosed for the separation of aromates from hydrocarbon mixtures employed as entry products, by means of extractive distillation, employing as selective solvent N-substituted morpholine, the substitutions of which display no more than 7 C atoms. The raffinate produced as top product of the extractive distillation is subjected to a distillation, whereby the produced sump product with a solvent content between 20–75% by weight and a temperature between 20°–70° C., is led into a separation container and there separated into a heavy and a light phase. The heavy phase is then recycled into the extractive distillation column, whereas the light phase is recycled into the raffinate distillation column.

8 Claims, 1 Drawing Figure

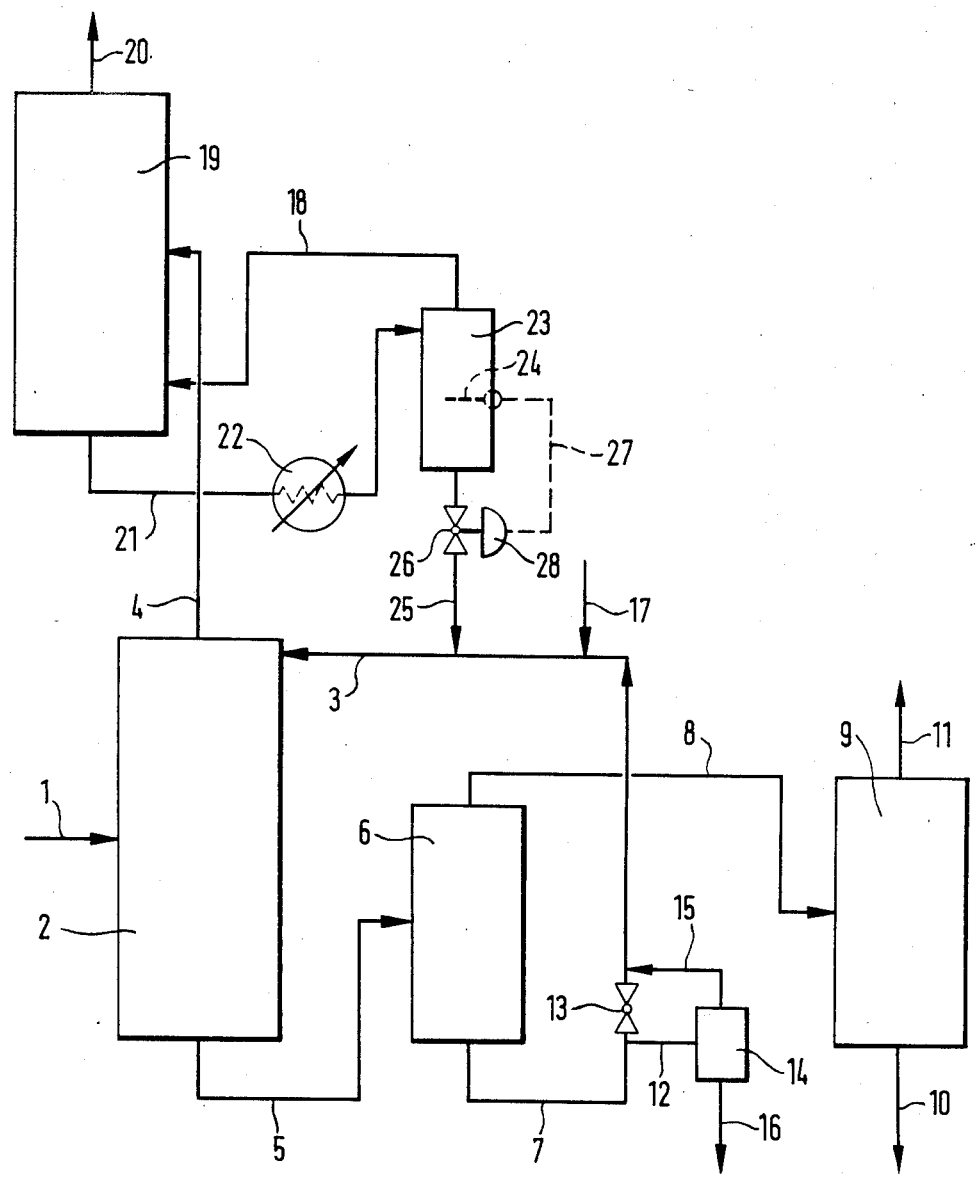

METHOD FOR THE SEPARATION OF AROMATES FROM HYDROCARBON MIXTURES CONTAINING AROMATICS

BACKGROUND OF THE INVENTION

The invention concerns a method for the separation of aromates from hydrocarbon mixtures of optional aromate content, mixtures which can contain as non-aromatic components, in particular, paraffins, cycloparaffins, olefins, diolefins as well as organic sulfur compounds. The separation occurs by means of extractive distillation in which N-substituted morpholine, the substitutions of which display no more than 7 carbon atoms, is employed as selective solvent, whereby the non-aromatic components of the hydrocarbon mixture, serving as an entry product are distilled off as raffinate across the top of the extractive distillation column. The aromates together with the employed solvent are discharged as extract from the sump of the extractive distillation column, and the raffinate is distilled for the purpose of recovery of the solvent residue present therein.

The above-described aromate recovery method has already been known for a number of years and has proven itself in practice, in various large-scale technical plants, particularly is the use of N-formylmorpholine as selective solvent. Herewith the sump product discharged from the extractive distillation column is normally led into a subsequently provided decanter, in which the aromates contained therein as extract are distillatively separated from the solvent. The solvent is then discharged from the sump of the decanter and reintroduced for repeat use in the extractive distillation column. Herewith the introduction and reintroduction of the solvent normally follows at the top of the extractive distillation column, for various process/technical reasons. However, it is practically unavoidable for the obtained raffinate to still contain a certain solvent residue whereby the solvent content in the raffinate can amount up to 2% by weight. For reasons of economy, and in view of a recovery of an as pure as possible raffinate, it is, however, indispensable to recover this solvent portion in the raffinate as extensively or completely as possible.

This would certainly be possible if one were to operate the extractive distillation columns with an appropriately high raffinate reflux. However, in contrast to normal distillation, such a reflux is unsuitable and, therefore, to be avoided with extractive distillation, for the following reasons:

1. A raffinate reflux leads to a dilution of the solvent and therewith to a decrease in selectivity, whereby the desired material separation is unnecessarily complicated.
2. Highly selective solvents—and the above-mentioned N-substituted morpholine belong to this category—display only a limited dissolving behavior for the non-aromatic hydrocarbons to be separated. A raffinate reflux can therefore lead to the formation of two liquid phases with different densities at the upper plate of the extractive distillation column, which makes a disturbance-free operation of the extractive distillation column impossible.

Accordingly, this suggested manner for the recovery of the solvent portion of the raffinate is eliminated and instead a separate recovery of the solvent from the raffinate must take place. This was previously performed by means of simple distillation of the raffinate in such a manner that the raffinate is discharged as top-product from the distillation column with a solvent content of less than 10 ppm, whereas the solvent, concentrated to nearly 100% purity, is discharged from the sump of this column and then led back into the extractive distillation column.

This manner of operation, with which an as complete as possible separation of raffinate and solvent is desired, promotes, however, a high apparatus expenditure (i.e., distillation column with a high number of plates) and a high energy consumption.

SUMMARY OF THE INVENTION

The invention is therefore based upon the object of so improving the above-described method for the distillative working up of the raffinate for the purpose of the separation and recovery of the solvent contained therein, that it can be performed with a lower apparatus expenditure and, in particular, with a lower energy consumption.

This object is attained according to the present invention by a method of the above-described type, which is characterized in that the sump product occurring upon the raffinate distillation is discharged with a solvent content of between about 20–75% by weight from the raffinate distillation column, and then by cooling down to a temperature of about 20°–70° C., led into a separation container and there separated into a heavy and a light phase, whereupon the heavy phase is led back into the extractive distillation column and the light phase is led back into the raffinate distillation column.

That is, with the method according to the present invention, one need not perform the concentration step of the solvent, during the raffinate distillation, to a purity of nearly 100%.

Such a complete separation of raffinate and solvent requires, in particular, that at the boiling point of the above-mentioned solvent lying between 200°–280° C., a heating vapor for the raffinate distillation column of at least 40–50 bar. By contrast, the method according to the present invention provides for driving the raffinate distillation only to the extent that a solvent content between 20–75% by weight has become present in the sump product of the raffinate distillation column. A direct recycling of this sump product into the extractive distillation column would generally be connected with considerable disadvantages since, in addition to the solvent and the aromates contained in the raffinate as impurities, the raffinate becomes enriched in non-aromatic hydrocarbons, which, based upon their boiling point characteristics and their chemical structures, are the most difficult to separate from the aromates in the extractive distillation column, and which therefore, require a particularly high ratio of solvent to entry product and increased amount of heating energy for the extractive distillation. Involved herewith are, indeed depending upon the composition of the entry product, primarily methylcyclohexane, certain isomers of dimethylcyclohexane as well as ethylcyclohexane.

It was surprising to discover, however, that the sump product with the above-mentioned solvent content, after cooling to a temperature of between 20°–70° C., separates into two phases in a separation container. Herewith the light phase (upper phase) becomes enriched in the above-mentioned critical hydrocarbons, whereas the heavy phase (lower phase) is composed essentially of the solvent and the aromates, which arrive in the raffinate as impurities. On account of the existing density difference, a sharp separation of both phases adjusts in the separation container. Based upon its favorable composition, the heavy phase can, therefore, be reintroduced into the extractive distillation column, without the disadvantages of the prior art. The light phase, in contrast, is reintroduced into the raffinate distillation column. This reintroduction follows, preferably, in the sump of the raffinate distillation column. The described manner of operation can, thereby, be performed as a continuous method, whereby the amount of the circulating light phase comes to a multiple of the discharged heavy phase.

The treatment in a separation container of the raffinate from the distillation processes is indeed known in principle, e.g., from German Offenlegungsschrift D.E-.O.S. No. 14 14 357. However, such a treatment previously served the exclusive purpose of separating from the hydrocarbons of the raffinate, the water which arrives in the raffinate as a result of the employment of water-containing solvents. This known manner of operation, therefore, provides no suggestion at all for the method according to the present invention.

The solvent content of the sump product from the raffinate distillation can be controlled by means of the sump temperature or the temperature of the column heating at the sump of the raffinate distillation column, since a clear connection exists between the solvent content and the sump temperature, in that with an increasing solvent content, the sump temperature rises, whereby the adjusting sump temperature is naturally dependent on the boiling temperature of the employed solvent and the composition of the hydrocarbon mixture to be worked up in the raffinate distillation column. Thus, for example, the recovery of benzene from a crude benzene fraction obtained from a pyrolysis benzene, by means of extractive distillation with N-formylmorpholine with a solvent content in the sump product of the raffinate distillation column of 50% by weight, the sump temperature adjusts to about 100° C. In contrast, if the content of the same solvent in the sump product amounts to about 75% by weight, the sump temperature will adjust to about 125° C. Obviously, instead of a temperature measurement, analytical methods can also be employed, e.g., gas chromatography, for determination and control of the solvent content of the sump product.

BRIEF DESCRIPTION OF THE DRAWINGS

The single FIGURE represents a flow scheme for the method according to the present invention, whereby only the apparatus parts required for illustration of the method are included, whereas additional arrangements, for example, pumps, heat exchanger and the like are not shown but may be employed.

The novel features which are considered characteristic of the invention are set forth, in particular, in the appended claims. The invention itself, however, both as to its construction and its method of operation, together with additional objects and advantages thereof, will be best understood from the following description of specific embodiments when read in conjuction with the accompanying drawing.

DESCRIPTION OF THE PREFERRED EMBODIMENTS

The hydrocarbon mixture serving as entry product, which if necessary may be subjected to a pre-distillation, is led through conduit 1 into the middle part of the extractive distillation column 2 provided with plates. The entry product is therewith either heated to near the boiling point, so that it evaporates upon entry into the extractive distillation column, or it can even be introduced already in an evaporated state into the extractive distillation column. The employed selective solvent is led into the extractive distillation column 2 at the top by means of conduit 3, and flows across the plates of this column from top to bottom, whereby it takes up to vaporous aromates. The non-aromatic hydrocarbons, which form the raffinate phase, escape by means of conduit 4 at the top of the column and are led across this conduit into the middle part of the raffinate distillation column 19, which is provided with packing material or plates.

The liquid sump product of the extractive distillation column 2 is composed of the solvent and the aromates dissolved therein, and is discharged from the extractive distillation column 2 by means of conduit 5, whereupon it is led into the decanter 6, in which the aromates are distillatively separated from the selective solvent. The solvent is removed from the column sump by means of conduit 7, and flows over conduit 3 back into the extractive distillation column 2, whereas the aromates escape at the top from the decanter column 6, and are led through conduit 8 into column 9, in which their further separation takes place. Thus, for example, by means of conduit 10, the higher boiling components can be discharged and by means of conduit 11, the lower boiling components. Because the employed solvent can become enriched with impurities over time, a branch conduit 12 is provided in the area of conduit 7, through which conduit 12, with appropriate adjustment of valve 13, a partial amount of the solvent can be led to the regeneration arrangement 14. The regenerated solvent is reintroduced into the circulation (i.e., conduit 7), by means of conduit 15, whereas the separated impurities are removed from the regeneration arrangement by means of conduit 16. Conduit 17 serves exclusively for the introduction of fresh solvent.

For performance of the method according to the present invention, the sump product produced in the raffinate distillation column 19 is discharged across conduit 21 with a solvent content of between about 20–75% by weight, whereas hydrocarbons of the raffinate, with a solvent content below 10 ppm are removed from the raffinate distillation column 19 across conduit 20. The sump product in conduit 21 is led across cooler 22, in which the required cooling down to a temperature between about 20°–70° C. takes place, into the separation container 23. Therewith the sump product enters tangentially into the upper part of the separation chamber 23, in the middle area of which is installed the interface regulator 24. Since the amount of sump product flowing across conduit 21 is relatively small, the cooler 22 is not necessary, it is moreover even possible to avoid this cooler device and perform the cooling down of the sump product in conduit 21 and in the separation container 23, which in this case would not be insulated but would be provided with a cooling jacket. Too strong a cooling down of the sump product to a temperature below 20° C. is not suitable because the heating energy requirement in the raffinate distillation column 19 and the extractive distillation column 2 would be unnecessarily increased. The desired separation of the introduced sump product into an upper and a lower phase follows in the separation container at a temperature of between about 20°–70° C. Compositions of both these phases have already been referred to above. The discharge of the heavy phase (lower phase) from separation container 22, is controlled by the interface regulator 24. This takes place in such a manner that the position of the interface between the heavy and the light phases influences the position of the interface regulator 24, which is fastened freely movable at a joint. As soon as the heavy phase in the lower part of the separation container 23 has become enriched to the extent that the interface between heavier and lower phases is located at the same height as the regulator 24, the regulator acquires the horizontal position represented in the drawing and upon obtaining this position, sets into operation the motor device 28 of vavle 26, by means of impulse conduit 27, so that the valve is opened. Since valve 6 is installed in conduit 25, the heavier phase can thereby be discharged from the separation container 23 and can be united by means of this conduit with the solvent flowing in conduit 3. In contrast, when the interface between heavier and lighter phases in the separation container sinks downward, the position of the interface regulator 24 changes correspondingly downward, and valve 26 is thereby closed or throttled in the described manner. The light phase (upper phase) is removed from the separation container 23 across conduit 18 and is led back into the sump of the raffinate distillation column 19. According to a deviation from the arrangement represented in the FIGURE, it is naturally also possible to not unite the heavy phase discharge through conduit 25 with the solvent in conduit 3, but to lead it separately therefrom into the upper part of the extractive distillation column 2.

The advantageous effect of the manner of operation according to the present invention is substantiated by means of the following comparison test. As entry product, a crude benzene fraction recovered from a hydrated pyrolysis benzene is employed, which is subjected to an extractive distillation with N-formylmorpholine. The non-aromate content in the entry product amounts to 25% by weight, while the methylcyclohexane content is 0.2% by weight. The methylcyclohexane is a key component determining the energy consumption in the extractive distillation column since an increase of the methylcyclohexane content in the entry product of about 0.1% by weight necessitates, according to the present invention, during the extractive distillation, an additional consumption of heat energy of 90 kJ per kg entry product.

The solvent content in the top product of the extractive distillation amounts to about 2% by weight. It is therefore necessary to subject this top product to a distillation for the purpose of solvent recovery. In the first part of the comparison test, the sump product of this so-called raffinate distillation, is recycled directly, i.e., without phase separation into the extractive distillation column, whereas in the second part of this comparison test, operated with phase separation according to the present invention, only the heavy phase separated in the separation container is recycled into the extractice distillation column. The following Table sets forth the most important data from both product streams recycled into the extractive distillation column.

TABLE 1

|  | Without phase separation | With phase separation |
|---|---|---|
| Non-aromates, esp. | 58.7% wt. | 8.5% wt. |
| methylcyclohexane | 12.1% wt. | 2.6% wt. |
| Aromates | 1.0% wt. | 1.0% wt. |
| N—formylmorpholine | 40.3% wt. | 90.5% wt. |
| Recyle amount per 1000 kg entry product | 13.2 kg | 5.9 kg |
| esp. methylcyclohexane | 1.6 kg | 0.15 kg |

A comparison of the data shows that by means of employment of the method according to the present invention with phase separation, the amount of methylcyclohexane recycled to the extractive distillation column is decreased from 1.6 kg to 0.15 kg. Accordingly, with the manner of operation of the present invention the heat consumption in the extractive distillation is reduced to 85% of the required amount of the previous manner of operation. Moreover, one must consider that with the manner of operation according to the present invention, the portion of the non-aromates recycled into the extractive distillation column is likewise substantially lowered, so that disturbances to the operation of the extractive distillation column resulting from a too high non-aromate reflux are excluded.

It will be understood that each of the elements described above, or two or more together, may also find a useful application in other types of separations differing from the types described above.

While the invention has been illustrated and described as embodied in a method for the separation of aromates from hydrocarbon mixtures of optional aromate content, it is not intended to be limited to the details shown, since various modifications and structural changes may be made without departing from the spirit and scope of the present invention.

Without further analysis, the foregoing will fully reveal the gist of the present invention so that others can, by applying the knowledge of one of ordinary skill in the art, readily adapt for various applications the present invention.

We claim:

1. Method for the separation of aromates from a hydrocarbon mixture of aromate content, which mixture can contain as non-aromatic components, particularly paraffins, cycloparaffins, olefins, diolefins, as well as organic sulphur compounds, by means of extractive distillation employing N-substituted morpholine, substitutions of which display no more than 7 C atoms, as selective solvent, whereby the non-aromatic component of the hydrocarbon mixture serving as entry product is distilled off as raffinate across the top of an extractive distillation column, while the aromates together with the employed solvent are discharged as extract from the sump of the extractive distillation column, and whereby the raffinate is distilled for the purpose of recovery of the solvent residue therein, comprising distilling the raffinate, thereby providing a sump product, discharging said sump product with a solvent content between about 20–75% by weight from the raffinate distillation column, cooling down said sump product to a temperature between about 20°–70° C., introducing said cooled sump product into a separation container, and separating the sump product in the separation container into a heavy phase and a light phase, thereupon reintroducing the heavy phase into the extractive distillation column and the light phase into the raffinate distillation column.

2. The method according to claim 1, wherein the sump product produced from the raffinate distillation is passed through a cooler before introduction into said separation container.

3. The method according to claim 1, wherein the heavy phase discharged from the separation container is reintroduced in admixture with solvent into the upper part of the extractive distillation column.

4. The method according to claim 1, wherein the heavy phase discharged from the separation container is reintroduced separately from solvent into the upper part of the extractive distillation column.

5. The method according to claim 1, wherein the light phase discharged from the separation container is reintroduced into the sump of the raffinate distillation column.

6. The method according to claim 1, further comprising controlling the discharge of the heavy phase from the separation container by means of a valve, position of said valve depending upon the level of an interface regulator disposed in said separation container so that when the interface level, being variable, is located at a height substantially equal to said interface regulator, thereby ensuring that the heavy phase has become sufficiently enriched with said solvent and aromates, said interface regulator opens said valve to discharge the heavy phase.

7. The method according to claim 1, further comprising distillatively separating aromates from solvent in said extract in a decanter.

8. The method according to claim 7, further comprising regenerating a partial amount of the solvent separated from said extract, and then reintroducing regenerated solvent into said extractive distillation column.

* * * * *